US011767289B2

(12) United States Patent
Jones et al.

(10) Patent No.: US 11,767,289 B2
(45) Date of Patent: *Sep. 26, 2023

(54) METHODS AND COMPOSITIONS FOR PEST CONTROL (71) Applicants: VMI Foundation, Lexington, VA (US); United States, as Represented by the Secretary of Agriculture, Washington, DC (US)

(72) Inventors: Tappey H. Jones, Staunton, VA (US); Robert Kenneth Vander Meer, Newberry, FL (US)

(73) Assignees: United States of America, as represented by the Secretary of Agriculture, Washington, DC (US); THE VMI FOUNDATION, Lexington, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/419,899

(22) Filed: Jan. 30, 2017

(65) Prior Publication Data

US 2018/0009740 A1  Jan. 11, 2018

Related U.S. Application Data (63) Continuation of application No. 13/883,204, filed as application No. PCT/US2011/059200 on Nov. 3, 2011, now Pat. No. 9,950,994.

(60) Provisional application No. 61/409,711, filed on Nov. 3, 2010.

(51) Int. Cl.
| C07C 235/74 | (2006.01) |
| A01N 37/18 | (2006.01) |
| A01N 37/36 | (2006.01) |
| A01N 37/42 | (2006.01) |
| C07C 233/18 | (2006.01) |
| C07C 235/08 | (2006.01) |

(52) U.S. Cl.
CPC ............ *C07C 235/74* (2013.01); *A01N 37/18* (2013.01); *A01N 37/36* (2013.01); *A01N 37/42* (2013.01); *C07C 233/18* (2013.01); *C07C 235/08* (2013.01)

(58) Field of Classification Search
CPC ................ C07C 235/74; C07C 235/08; C07C 233/18; A01N 37/42; A01N 37/18; A01N 37/36
See application file for complete search history.

(56) References Cited

U.S. PATENT DOCUMENTS

| 3,957,905 A | 5/1976 | Sumoto et al. |
| 4,013,618 A | 3/1977 | Tsuji et al. |
| 2006/0110343 A1 | 5/2006 | Lintner |
| 2009/0099135 A1 | 4/2009 | Enan |

OTHER PUBLICATIONS

International Search Report and Written Opinion in International Application No. PCT/US2011/059200, dated Jun. 25, 2012, 12 pages.
International Preliminary Report on Patentability in International Application No. PCT/US2011/059200, dated May 16, 2013, 8 pages.
Adams et al., "Male specific tyramides from three additional myrmicine genera," *Biochem, Sys. Ecol.*, Mar. 2010, 38:454-456.
Attygalle and Morgan, "Chemicals from the glands of ants," *Chem. Soc. Rev.*, 1984, 13:245-278.
Ayasse et al., "Mating Behavior and Chemical Communication in the Order Hymenoptera," *Ann. Rev. Entomolo.*, Jan. 2001, 46:31-78.
Barron et al., "Comparing injection, feeding and topical application methods for treatment of honeybees with octopamine," *J. Insect Physiol.*, Feb. 2007, 53(2)487-194.
Beggs et al., "Queen pheromone modulates brain dopamine function in worker honey bees," *Proc Natl Acad Sci.*, Feb. 7, 2007, 104:2460-2464.
Blum et al., "Chemistry of the mandibular gland secretion of the ant *Camponotus vagus*," *M. Compo Biochem. Physiol. Part B*, 1987, 86(2):251-252.
Bolton, "Synopsis and Classification of Formicidae," Mem. Am. Entomol. Inst., 2003, 71: 370pp (Table of Contents Only).
Boomsma et al., "The Evolution of Male Traits in Social Insects," *Annu. Rev. Entomol.*, Jan. 2005, 50:395-420.
Boroczky et al. "Cluster Analysis as Selection and Dereplication Tool for the Identification of New Natural Compounds from Large Sample Sets," *Chem. Biodiv.*, Jun. 23, 2006, 3:622-634.
Boulay et al., "Odour convergence and tolerance between nestmates through trophallaxis and grooming in the ant *Camponotus fellah* (Dalia Torre)," *Insect Soc*, 2004, 51:55-61.
Brady et al., "Evaluating alternative hypotheses for the early evolution and diversification of ants," *Proc. Natl. Acad. Sci. U.S.A.*, Nov. 28, 2006, 103(48):18172-18177.
Brand et al., "Caste-Specific Compounds in Male Carpenter Ants," *Science*, Jan. 26, 1973, 179:388-389.
Briese, "Different Modes of Reproductive Behaviour (including a Description of Colony Fission) in a Species of *Chelaner* (Hymenoptera: Formicidae)," Insectes Sociaux, 1983, 30(3):308-316.
Cahan et al., "Reproductive Division of Labor Between Hybrid and Nonhybrid Offspring in a Fire Ant Hybrid Zone," Evolution, 2003, 57(7):1562-1570.
Daly et al., "Indolizidine 239Q and quinolizidine 275I. Major alkaloids in two Argentinian bufonid toads (*Melanophiyniscus*)," *Toxicon*, Dec. 15, 2008, 52:858-870.
Deslippe and Guo, "Venom alkaloids of fire ants in relation to worker size and age," *Toxicon*, Feb. 2000, 38(2):223-232.
Farooqui et al., "Octopamine receptors in the honeybee (*Apis mellifera*) brain and their disruption by RNA-mediated interference," *J. of Ins. Physiol.*, Aug. 2004, 50(8):701-713.
Fowler, "Male induction and function of workers' excitability during swarming in leaf-cutting ants (*Atta* and *Acromyrmex*) (Hymenoptera, Formicidae)," *Int. J. Invert. Reprod.*, 1982, 4:333-335.

(Continued)

*Primary Examiner* — Yong S. Chong
(74) *Attorney, Agent, or Firm* — Fish & Richardson P.C.

(57) ABSTRACT

Methods and compositions for pest control, and more particularly for control of ants, e.g., of the subfamily Myrmicinae, using tyramides.

8 Claims, 5 Drawing Sheets

(56) References Cited

OTHER PUBLICATIONS

Franks et al., "Nuptial flights and calling behavior in the anti *Leptothorax acervorum*(Fabr)," *Insect. Soc.*, 1991, 38:327-330.

Fussnecker et al., "Octopamine and tyramine influence the behavioral profile of locomotor activity in the honey bee (*Apis mellifera*)," *J. of Ins. Physiol.*, Oct. 2006, 52:1083-1092.

Halmekoski and Pekkala, "Selective n-Butrylations of some Adrenergic Amines," *Acta Pharm. Fenn.*, 1977, 86:209-214.

Halmekoski et al., "Selective Propionylations of some Adrenergic Amines," *Acta Pharm. Fenn.*, 1979, 88:73-78.

Heinze et al., "Reproductive behavior of the ant*Leptothorax* (Dichothorax) *pergandei*," *Insectes Soc.*, 1995,42:309-315.

Holldobler and Bartz, "Sociobiology of reproduction in ants," *Forts. Zool.*, 1985, 31:237-257.

Holldobler and Carlin, "Anonymity and specificity in the chemical communication signals of social insects," *J Comp Physiol A.*, 1987, 161:567-581.

Janusz et al., "Vanilloids. 1. Analogs of capsaicin with antinociceptive and antiinflammatory activity," *J. Med. Chem.*, 1993, 36:2595-2604.

Jones et al., "Chemistry of venom alkaloids in the ant *Megalomyrmex foreli* (Myrmicinae) from Costa Rica," *J. Chem. Ecol.*, 1991, 17:2507-2517.

Jones et al., "Primary Tetradecenyl Amines from the Ant *Monomorium floricola*," *J. Nat. Prod.*, 1996, 59:801-802.

Jones et al., "Venom Chemistry of the Ant *Myrmicaria melanogaster* from Brunei," *J. Nat. Prod.*, 2007, 70:160-168.

Jones et al., "Caste-Specific Tyramides from Myrmicine Ants," *J. Nat. Prod.*, Jan. 2010, 73:313-316.

Jones and Blum, "Ant venom alkaloids from *Solenopsis* and *Monorium* species: Recent developments," *Tetrahedron* 1982, 38:1949-1958.

Kenne and Dejean, "Nuptial Flight of Myrmicaria opaciventris (Hymenoptera: Formicidae, Myrmicinae)," *Sociobiology*, 1998, 31:41-50.

Lessard et al., "Invasive ants alter the phylogenetic structure of ant communities," *Ecology*, 2009, 90:2664-2669.

Linn et al., "Effects of photoperiod on the circadian timing of pheromone response in male Trichoplusia ni: Relationship to the modulatory action of octopamine," *J Insect Physiol*, Sep. 1996, 42:881-891.

Menzel and Muller, "Learning and Memory in Honeybees: From Behavior to Neural Substrates," *Ann Rev Neurosci*, Mar. 1996, 19:379-404.

Noordijk et al., "How ants find each other; temporal and spatial patterns in nuptial flights," *Insect. Soc.*, 2008, 55:266-273.

Numata and Ibuka, "Chapter 6 Alkaloids from Ants and Other Insects," *The Alkaloids*, 1987, 31:193-315.

Porter and Savignano, "Invasion of Polygyne Fire Ants Decimates Native Ants and Disrupts Arthropod Community," *Ecology*, 1990, 71:2095.

Ritter et al., "5-methyl-3-butyl-octahydroindolizine, a novel type of pheromone attractive to Pharaoh's ants (*Monomorium pharaonis* (L.)," Experientia, 1973, 29(5):530-531.

Robertson and Villet, "Mating behaviour in three species of myrmicine ants (Hymenoptera: Formicidae)," *J. Nat. Hist.*, 1989, 23:767-773.

Robinson et al., "Neurochemicals aid bee nestmate recognition," *Nature*, Jun. 10, 1990, 399:534-535.

Roeder, "Tyramine and Octopamine: Ruling Behavior and Metabolism," *Ann. Rev. Entomol.*, Jan. 2005, 50:447-477.

Schroder et al., "A new family of tricyclic alkaloids from Myrmicaria ants," *Tetrahedron*, Oct. 1996, 52:13539-13546.

Shin et al., "Synthesis of Optically Active Phthaloyl d-Aminooxy Acids from 1-Amino Acids or 1-Hydroxy Acids as Building Blocks for the Preparation of Aminooxy Peptides," *J. Org. Chem.*, 2000, 65:7667-7675.

Smith et al., "Ants (Formicidae): Models for Social Complexity," *J. Cold Spring Harb. Protoc.*, 2009, 4:1-13.

Snelling, "Two New Species of Thief Ants (*Solenopsis*) From Puerto Rico (Hymenoptera: Formicidae)," *Sociobiology*, 2001, 37:511-525.

Spande et al., "Occurrence and Significance of Decahydroquinolines from Dendrobatid Poison Frogs and a Myrmicine Ant: Use of 1H and 13C NMR in Their Conformational Analysis," *J. Nat. Prod.*, 1999, 62:5-21.

Torres et al., "Caste Specific Alkaloid Chemistry of Solenopsis maboya and S. torresi (Hymenoptera: Formicidae)," Sociobiology, 2001, 37, 579-583.

Vander Meer and Morel, "Nestmate recognition in ants," *Pheromone Communication in Social Insects*, 1998, 79-103.

Vander Meer and Preston, "Queen regulates biogenic amine level and nestmate recognition in workers of the fire ant, *Solenopsis invicta*," *Naturwissenschaften*, 2008, 95:1155-1158.

Velusamy and Punniyamurthy, "Novel Vanadium-Catalyzed Oxidation of Alcohols to Aldehydes and Ketones under Atmospheric Oxygen," *Org. Lett.*, 2004, 6:217-219.

Castro et al., "Antioxidant activity of liquors from steam explosion of Olea europea wood," Wood Science and Technology, Oct. 2008, 42:579-92.

METHODS AND COMPOSITIONS FOR PEST CONTROL

CLAIM OF PRIORITY

This application is a continuation of and claims the benefit of U.S. application Ser. No. 13/883,204, filed Jun. 14, 2013, which claims the benefit of U.S. national stage under 35 USC § 371 of International Application Number PCT/US2011/059200, filed on 3 Nov. 2011, which claims the benefit of U.S. Provisional Patent Application Ser. No. 61/409,711, filed on Nov. 3, 2010, the entire contents of which applications are hereby incorporated by reference.

JOINT RESEARCH AGREEMENT

This invention was made pursuant to a joint research agreement between the VMI Research Laboratories and the United States Department of Agriculture.

TECHNICAL FIELD

This invention relates to methods and compositions for pest control, and more particularly to control of ants, e.g., of the subfamily Myrmicinae, using naturally-occurring N-acyltyramines (tyramides).

BACKGROUND

It has been estimated that there are over 20 thousand ant species (Hölldobler and Wilson, The Ants. Harvard University Press, Cambridge, 1990; Smith et al., Cold Spring Harb. Protoc. 4:1, 2009), over 12,500 currently described (antbase.org, 15 Jan. 2010) some of which play a large role in destroying (Lessard et al., Ecology 90:2664, 2009; Porter and Savignano, Ecology 71:2095, 1990) or maintaining the structure of ecological communities (Hölldobler and Wilson, 1990). The Myrmicinae subfamily is the largest of the 21 extant subfamilies in the ants (Hymenoptera: Formicidae) (Bolton, Mem. Am. Entomol. Inst. 71:1, 2003). The Myrmicinae subfamily includes about 140 genera within the group, including species with a functional sting (such as ants in the genus *Solenopsis*, one of which is *S. invicta*, known as the "red imported fire ant," and *Myrmica rubra*, also known as the European fire ant or common red ant, a species of ant of the genus *Myrmica*), and fungus-growing ants (of the tribe Attini) that include leafcutter ants (genus *Atta* and genus *Acromyrmex*). These ants are considered pests in commercial, agricultural, and residential settings, causing significant damage and injury to plants and animals alike. For example, *M. pharaonis* is described as "a pest in heated buildings, bakeries, etc. in many non-tropical countries . . . they carry pathogenic bacteria, have the capacity to transmit disease and are able to enter even highly sophisticated isolation units." See Beatson, Lancet 2: 435 (1872).

Ants use a complex chemosensory system involving a mixture of semiochemicals for within and between species interactions (i.e., recruitment, nestmate recognition, alarm, territorial marking, competition, etc.) (Attygalle and Morgan, Chem. Soc. Rev. 13:245, 1984; Holldobler and Carlin, J Comp Physiol A. 161:567, 1987). Many of the glandular substances are small volatile molecules and although many still need to be studied to determine their function, a large number have been identified (Attygalle and Morgan, 1984).

SUMMARY

At least in part, the present invention is based on the discovery of certain tyramide compounds present only in males ants of the subfamily Myrmicine. Thus, the present invention includes compositions comprising those compounds, and methods of using the same for pest control.

Thus in one aspect, the invention provides compositions comprising one or more compounds, e.g., substantially purified compounds, of the formula and salts thereof, e.g., sodium, potassium and ammonium or amine salts.

In another aspect, the invention provides compositions comprising a compound, e.g., a substantially purified compound, of the formula and salts thereof, e.g., sodium, potassium and ammonium or amine salts.

In a further aspect, the invention provides compositions comprising one or more compounds, e.g., substantially purified compounds, of a formula selected from the group consisting of Formula I Formula II -continued

C

Formula III wherein R and R' can be a branched, unbranched, cyclic, polycyclic, or unsaturated carbon or cyclic ether moiety up to twenty carbons, e.g., up to 12 carbons, up to 10 carbons, or up to five carbons, or a salt thereof, e.g., sodium, potassium and ammonium or amine salts, in combination with another compound, e.g., an ant-attractant component, an ant-toxic component, or both.

In some embodiments, the compound has the formula wherein R is methyl, ethyl, n-pentyl, n-propyl, isopropyl, —C(═O)CH$_2$CH(CH$_3$)$_2$, sec-butyl, or tert-butyl.

Also provided herein are containers including a composition described herein in a container, e.g., any man-made object that can hold things, such as a vial, bottle, can, box, cup, bag, blister pack, etc.

In some embodiments, the composition and/or the compound is in a solid, liquid, or semi-solid form.

In some embodiments, the composition and/or the compound is a spray, powder, granule, tablet, gel, cream, or lotion.

In some embodiments, the composition is substantially purified.

Also provided herein is the use of a composition described herein in a method of controlling ants, compositions descried herein for use in a method of controlling ants, and devices for ant control comprising a composition described herein.

In some embodiments, the ants are imported fire ants (*S. invicta*) or leafcutter ants (*Atta* sp.).

In a further aspect, the invention provides methods for controlling ants using the compounds and/or compositions described herein. In some embodiments, the methods include delivering an effective amount of a composition comprising one or more compounds of a formula selected from the group consisting of

A

Formula I

-continued

B

Formula II

C

Formula III wherein R and R' can be a branched, unbranched, cyclic, polycyclic, or unsaturated carbon or cyclic ether moiety up to twenty carbons, e.g., up to 12 carbons, up to 10 carbons, or up to five carbons, or a salt thereof.

In some embodiments, the compound has the formula wherein R is methyl, ethyl, n-pentyl, n-propyl, isopropyl, —C(═O)CH$_2$CH(CH$_3$)$_2$, sec-butyl, or tert-butyl.

In some embodiments, the composition further includes an ant-attractant component, an ant-toxic component, or both.

In some embodiments, the ants are imported fire ants (*S. invicta*) or leafcutter ants (*Atta* sp.).

In some embodiments of the uses, devices, or methods described herein, the compound disrupts reproduction.

As used herein, a "substantially purified compound" is at least 5% pure, e.g., weight/weight, e.g., 10%, 15%, 20%, 25%, 30%, 40%, 50%, 60%, 70%, 75%, 80%, 90%, 95%, or about 100% weight/weight of a total composition.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

In invertebrates, the biogenic amines, octopamine (OA) and tyramine (TA) are functional homologs to the vertebrate adrenergic neurotransmitters, noradrenaline and adrenaline (Roeder, Ann. Rev. Entomol. 50:447-477, 2005). Together they coordinate an insect's response to outside stimuli. Neuromodulatory biogenic amines have been shown to have several critical developmental and reproductive functions in insects. Tyramides are analogues of tyramine, thus it is informative to outline the functions of biogenic amines, including tyramine. In insects, OA and TA acts as a neurotransmitter and/or neuromodulator, and many sensory inputs, including olfactory, have been reported (Roeder, Ann. Rev. Entomol. 50:447-477, 2005). Interestingly, OA increases pheromone acuity in insects by lowering the threshold of response, e.g. male moths are more sensitive to the female sex pheromone in the presence of OA (Linn et al., J Insect Physiol 42:881-891, 1996). In addition, the lower threshold was found to be for pheromone specific neurons, rather than neurons for general odors.

In social insects OA and TA have been shown to influence locomotor activity of honey bees (Fussnecker et al., J. of Ins. Physiol. 52: 1083-1092, 2006). OA has been shown to be involved in honey bee associative learning (Menzel and Müller, Ann Rev Neurosci 19:379-404, 1996), honey bee dance behavior (Barron et al., J. Insect Physiol. 53:187-194, 2007), Honey bee queen pheromone has been shown to influence worker dopamine (DA) levels, which influences worker behavior (Beggs et al., Proc Natl Acad Sci 104:2460-2464, 2007). Importantly, OA was indirectly implicated in nestmate recognition in honey bees when treatment with OA agonists improved discrimination of nestmates from non-nestmates (Robinson et al., Nature 399:534-535, 1999). Nestmate recognition is critical to social insect organization, providing a means to maintain territoriality and close the colony to parasites and predators. Ants detect the colony chemical label via their antennae and respond to the label mismatch of an intruder with aggressive behavior (Vander Meer and Morel, "Nestmate recognition in ants." In: R. K. Vander Meer, Breed M., Winston M., Espelie K. E., editors. *Pheromone Communication in Social Insects.* Boulder, Colo. 368 p.: Westview Press. p 79-103 1998). In the fire ant, worker ability to recognize conspecific non-nestmates decreases if the colony queen is removed, such that they do not recognize conspecific non-nestmates as different (Vander Meer and Alonso, Behav. Ecol. Sociobiol. 51:122-130, 2002). A new analysis method for OA was developed (Barron et al., J. Insect Physiol. 53:187-194, 2007) and used to test the hypothesis that neuromodulator, OA, affects nestmate recognition acuity in workers. The queenless workers exhibit reduced brain OA levels and reduced discriminatory acuteness; however, feeding queenless workers octopamine restored both. This was the first demonstration of a link between the colony queen, a worker biogenic amine, and conspecific nestmate recognition, a powerful expression of colony cohesion (Vander Meer et al., Naturwissenschaften 95:1155-1158, 2008). The only other report linking OA and behavior in ants is that OA inhibited isolation-induced trophallaxis (exchange of fluids between colony members through regurgitation) in *Camponotus fellah* workers (Boulay et al., Insect Soc 51:55-61, 2000). However, it is clear from the literature that there are numerous potential roles for biogenic amines in social insects, including the fire ant (Roeder, Ann. Rev. Entomol. 50:447-477, 2005).

The many key functional roles biogenic amines play in development and social insect specific activities. Disruption of normal receptor function is expected to deleteriously affect their functions in fire ants. OA receptors have been well characterized for other insects and specific agonists and antagonist are known (Roeder, Ann. Rev. Entomol. 50:447-477, 2005). In addition, RNA interference of honey bee OA receptors has been demonstrated (Farooqui et al., J. of Ins. Physiol. 50:701-713, 2004). Essential next steps in this progression are further defining biogenic amine functions including tyramides, and characterization of receptors.

Imported fire ants infest more than 320 million acres in 13 southern tier states and Puerto Rico and are spreading northward (APHIS 2007). This invasive ant is estimated to be responsible for almost $7 billion annually in damage repair, medical care, and control costs. The affected economic sectors are broad ranging and include households, electric service and communications, agriculture, schools and recreation areas (Lard et al., The Economic Impact of Red Imported Fire Ants in Rural Texas, 2006, available on the internet at fireantecon.tamu.edu/Publications/Rural%20Texas %20Fire %20Ant %20Survey %2012-1-06%20.pdf). As is the case for most exotic species, invasive fire ants were introduced without most of their natural enemies in their native South American range. As a consequence, fire ant populations in the United States are 5-10 times denser than in South America (Porter et al., Environmental Entomology 26: 373-384, 1997). Interestingly, ants comprise 5% of the world's 100 worst invasive alien species, and of the 17 land invertebrates listed, 28% are ants, including fire ants. In the last decade, *S. invicta* has changed from an invasive pest ant in the United States to a global problem, with infestations occurring in Australia (Henshaw et al., Australian Journal of Entomology. 44:37-44, 2005), Taiwan (Chen et al., Environ. Entomol. 35:167-172, 2006), mainland China (Zeng et al., Chinese Bulletin of Entomology, 42:144-148, 2005, Zhang et al., Florida Entomologist 90: 723-731, 2007), Mexico (Sanchez-Pella et al., Entomological News, 116:363-366, 2005) and many Caribbean Island countries (Davis et al., Florida Entomologist, 84:735-736, 2001). Increasing global commerce ensures that not just fire ants, but other invasive ant species will be distributed to compatible habitats throughout the world, e.g. Argentine ant, the little fire ant, and the crazy ant (all of which are among the 100 worst invasive alien species).

Ant colonies generally reproduce by producing sexuals that mate in what is called a nuptial flight. During the nuptial flight, the males typically take flight before the females. Males then find a suitable mating ground and secrete a mating pheromone that the females follow. Ant mating behavior can generally be divided into two main categories: female-calling and male-aggregation. In female-calling syndrome, females attract males by releasing a pheromone. In male-aggregation syndrome, males produce an aggregation pheromone that results in the formation of swarms of males to which females are attracted. (See, e.g., Robertson and Villet, J. Nat. Hist. 23:767-773 (1989); Holldobler and Bartz, Forts. Zool. 31:237-257 (1985), pp. 237-257; Boomsma et al., Annu. Rev. Entomol. 50:395-420 (2005)). Some species of ants primarily do one or the other, while some do both (Franks et al., Insect. Soc. 38:327-330 (1991)).

In most ant species, new colonies are initiated by claustral foundation. In claustral foundation, a queen establishes a nest cell after a nuptial flight and rears the first brood on the food reserves of her own body. Alternatively, the colony may reproduce by fission, a process somewhat like swarming in which the queens take some worker ants with them to gather food and care for the brood. Some species may employ both strategies depending on environmental factors (Briese, Insectes Sociaux, Paris, 30(3):308-316 (1983)).

In both cases, the ants rely to some extent on chemical or hormonal cues to know when to emerge from the colony, when to initiate the nuptial flight, and how to find the ants of the opposite sex to initiate mating (pheromones are produced either by the male (male-aggregation syndrome) or the female (female-calling syndrome) (Holldobler and Bartz, (1985) supra; Bourke & Franks, *Social Evolution in Ants*. Princeton University Press, Princeton, N.J. (1995); Heinze et al, Insectes Soc. 42:309-315 (1995); Ayasse et al., Ann. Rev. Entomolo. 46:31-78 (2001)). Compounds specific to either sex of ants may play a role at some point in this process, or in other gender-specific behaviors such as the worker excitation/aggression that drives them to protect the sexuals during the nuptial flight or to protect their territory (destroying queens establishing new colonies too near the home colony) (Fowler, Int. J. Invert. Reprod., 4:333-335 (1982). Isolation and identification of gender-specific compounds thus provides methods for manipulating ant mating behavior, e.g., for initiating emergence or mating, and for controlling ant populations in sensitive areas.

The present inventors have discovered a group of tyramide compounds that are present in the gaster of male myrmicine ants, but not found in females. These compounds have the general structure of:

Formula I

A

Formula II

B

Formula III

C wherein R can be a branched, unbranched, cyclic, polycyclic, or unsaturated carbon or cyclic ether moiety up to twenty carbons, e.g., up to 12 carbons, up to 10 carbons, or up to five carbons. In some embodiments the compounds are α-hydroxyl tyramides of the general structure of Formula II, or α-keto tyramides of the general structure of Formula III wherein R' can be a branched, unbranched, cyclic, polycyclic, or unsaturated carbon or cyclic ether moiety up to twenty carbons, e.g., up to 12 carbons, up to 10 carbons, or up to five carbons. As one of skill in the art will appreciate, depending on the type and number of substituents, certain of the compounds of the formulas A, B, or C may be present as geometrical and/or optical isomers or regioisomers or as mixtures of these isomers in varying composition. The compositions described herein can include pure isomers and/or isomer mixtures.

In some embodiments, R or R' can be: methyl, ethyl, n-pentyl, n-propyl, isopropyl, —C(=O)CH$_2$CH(CH$_3$)$_2$, sec-butyl, or tert-butyl.

In some embodiments, the compositions described herein include two or more of these compounds.

Figure 1:
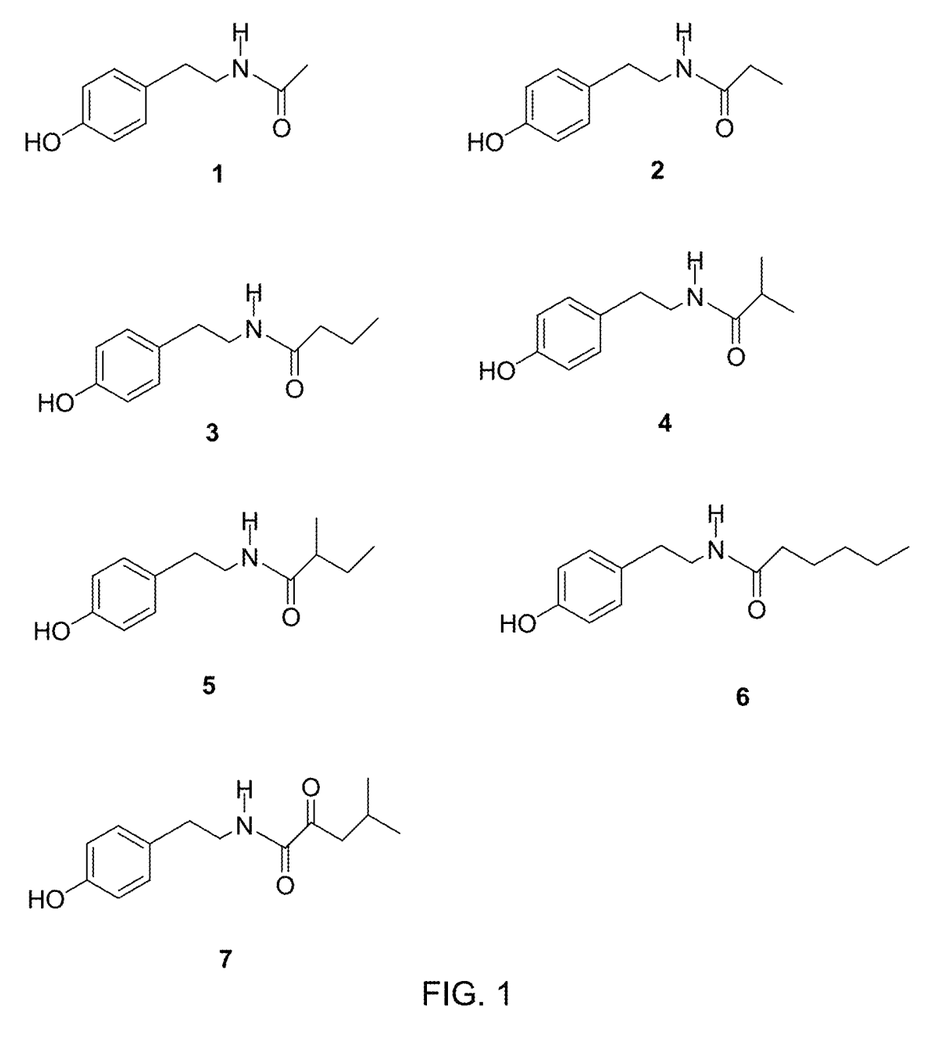
FIG. 1 shows the structure of seven specific compounds (1-7) described herein.

A number of exemplary compounds are shown in FIG. 1. Compound numbers used throughout the present application refer to the compounds as shown in FIG. 1, unless otherwise noted.

Thus the present invention includes the tyramide compounds, compositions and devices including the tyramide compounds, and methods of using the same for pest control.

Methods of Synthesizing

A number of synthetic methods known in the art can be used to make the compounds of the present invention. For example, compounds of formula A can be prepared by treating a mixture of tyramine and a slight excess of a suitable aqueous base such as dilute sodium hydroxide with two equivalents of the appropriate carboxylic chloride (R—COCl). After a suitable amount of time (depending on the nature of R, a few hrs to overnight) the mixture is extracted with a solvent such as methylene chloride. The methylene chloride solution is dried, and the solvent is removed. The residue is taken up in methanol and heated to reflux for a suitable amount of time. The solvent is removed in vacuo and compound A is separated from the ester (R—CO—OCH$_3$) by the appropriate chromatography or by extraction of the tyramide with hydroxide and reacidifying. As one of skill in the art will appreciate, the methods can be optimized depending on the R group desired. For example, if the R is small, a vacuum pump will remove the ester.

As another example, compounds of formula B can be prepared by treating an equivalent mixture of tyramine and the appropriate α-hydroxy carboxylic acid (R'—CHOH—COOH) in a polar aprotic solvent such as DMF with a coupling reagent such as DCC, EDCI, or a carboxylic activating agent such as TBTU, HATU, or DEPBT. After a suitable amount of time the mixture is worked up in the manner appropriate to the particular coupling method employed.

As yet another example, compounds of formula C can be prepared from compounds in class B by warming a toluene solution to 90° C. in the presence of a catalyst such as $V_2O_5$. Subsequent filtration and removal of the solvent in vacuo provides a product that is essentially pure or may be purified by chromatography.

Methods, Compositions and Devices for Pest Control

As described herein, tyramides are analogues of tyramines, neuromodulatory biogenic amines that have been shown to have critical developmental and reproductive functions in insects. The occurrence of these tyramides almost exclusively in males of the species examined (and exclusively in the external genitalia), as well as the apparent transfer of the tyramides from the males to the females, suggests that they have a function in regulating some aspect of mating behavior in these ants; a fair amount of field research already exists that indicates a role for the involvement of previously unknown pheromones (Smith et al., J. Cold Spring Harb. Protoc. 2009, 4, 1-13). The compounds described herein are expected to provide ant control by disrupting the mating process, thereby controlling ant populations. Without wishing to be bound by theory, the compounds may work by marking the females as mated (in the wild, the compounds may have the function of inhibiting second or multiple mating), and thereby discouraging males from mating with them. In some embodiments, the compositions are used (e.g., applied or devices are deployed) prior to, e.g., one month before, two weeks before, one week before, or 96, 72, 48, or 24 hours before, the annual mating time of the ants.

The compounds described herein can be incorporated into compositions and devices useful in controlling insect pests, e.g., ants, e.g., ants of the subfamily Myrmicinae, using naturally-occurring N-acyltyramines (tyramides). For example, the compounds described herein can be incorporated into a composition for application to the environment of the pest, optionally with an agriculturally suitable carrier comprising at least one of a liquid diluent, a solid diluent or a surfactant.

The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be encapsulated or microencapsulated and further formed into a suspension or solid formulation; alternatively the entire formulation of active ingredient can be encapsulated or microencapsulated, e.g., to control or delay release of the active ingredient. Sprayable formulations can be suspended in suitable media and used at preferred spray volumes, e.g., from about one to several hundred liters per hectare. High-strength compositions are primarily used as intermediates (e.g., concentrates) for further formulation (e.g., by dilution).

Solid diluents are known in the art, e.g., as described in Watkins, et al., *Handbook of Insecticide Dust Diluents and Carriers*, 2nd Ed., Dorland Books, Caldwell, N.J. Exemplary solid diluents can include, for example, clays such as bentonite, montmorillonite, attapulgite and kaolin, starch, sugar, silica, talc, diatomaceous earth, urea, calcium carbonate, sodium carbonate and bicarbonate, and sodium sulfate.

Liquid diluents are known in the art, e.g., as described in Marsden, *Solvents Guide*, 2nd Ed., Interscience, New York, 1950. Exemplary liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tong, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Surfactants are known in the art, e.g., as described in McCutcheon's *Detergents and Emulsifiers Annual*, Allured Publ. Corp., Ridgewood, N.J.; and in Sisely and Wood, *Encyclopedia of Surface Active Agents*, Chemical Publ. Co., Inc., New York, 1964. Surfactants can include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers.

In some embodiments, the formulations described herein can contain minor amounts of additives to reduce foam, caking, corrosion, microbiological growth and the like, or thickeners to increase viscosity.

Methods for preparing the formulations described herein are known in the art. For example, solutions, including emulsifiable concentrates, can be prepared by simply mixing the ingredients. Dusts and powders can be prepared, e.g., by blending and, optionally grinding, e.g., using a hammer mill or fluid-energy mill. Suspensions can be prepared, e.g., by wet-milling; see, for example, U.S. Pat. No. 3,060,084. Granules and pellets can be prepared, e.g., by spraying the active material upon preformed granular carriers or by agglomeration techniques. See, e.g., Browning, Chem. Eng., p 14748, (1967); Perry's *Chemical Engineer's Handbook*, 4th Ed., McGraw-Hill, New York, 1963, pages 8-57 and following, and PCT Publication WO 91/13546. Pellets can be prepared using methods known in the art, e.g., as described in U.S. Pat. No. 4,172,714. Water-dispersible and water-soluble granules can be prepared, e.g., as taught in U.S. Pat. Nos. 4,144,050, 3,920,442 and DE 3,246,493. Tablets can be prepared, e.g., as taught in U.S. Pat. No. 5,180,587 or 5,232,701 and U.S. Pat. No. 5,208,030. See also Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. Nos. 7,696,233 and 6,245,816.

In one example, the composition can be delivered in a solid, e.g., as pellets or powder formulation; a semi-solid, e.g., a gel or gellable formulation, e.g., as part of an ant trap; or in a liquid formulation, e.g., in a spray format, and can be used, e.g., to attract or repel ants from a selected area.

In some embodiments, the composition can be provided in a delayed-release composition, so that the composition is released over time. Suitable compositions are known in the art.

In some embodiments, the compounds described herein can be formulated with other ingredients, e.g., ant-attractant ingredients such as ant food (e.g., carbohydrates, cellulose, fats, proteins, and/or any other nutritional components) (see, e.g., U.S. Pat. Nos. 5,152,096; 5,939,061; 6,916,469; and 7,048,918. The compounds described herein can be formulated, e.g., as part of an ant bait to deliver an ant toxin for extermination of pest insects. A number of ant toxins are known in the art, including Thiamethoxam (Syngenta Crop Protection, Greensboro, N.C.); DOT; growth regulators; orthoboric acid; borates (e.g., sodium tetraborate); abamectin B1 (Whitmire Micro-Gen Research Laboratories, Inc.); fipronil (2-Phenethyl Propionate); Sulfluramid; Imidacloprid (Bayer Environmental Science, Montvale, N.J.); indoxacarb (Dupont, Wilmington, Del.); O,S-Dimethyl Acetylphosphoramidothioate; 2-phenethyl propionate; piperonyl butoxide; pyrethrins (e.g., permethrin, deltamethrin, tetramethrin, or Lambda-cyhalothrin [1α(S*),3α(Z)]-(±)-cyano-(3-phenoxyphenyl)methyl-3-(2-chloro-3,3,3-trifluoro-1-propenyl)-2,2-dimethylcyclopropanecarboxylate); or Cry toxin (U.S. Pat. No. 6,797,490). The toxin can be delivered with the compounds described herein, e.g., as part of a single composition, or can be delivered before or after delivery of the compounds described herein.

In some embodiments, the compounds described herein are used with an insect trap, e.g., to attract and trap insects, e.g., for pest control or to detect new or ongoing infestations. The traps can optionally include means for preventing the insect from escaping the trap, e.g., mechanical (a design that physically prevents the insect from leaving, such as a pattern that only allows ingress but not egress, or an edge or flange that prevents escape) or chemical (e.g., an adhesive or liquid that traps the insect) means.

The compounds and compositions described herein can be used in, or combination with, a number of devices known in the art for trapping, controlling, or exterminating ants, e.g., as described in U.S. Pat. Nos. 6,966,145, 6,609,330, 6,796,082, 6,283,064, 6,655,079, 6,474,015, 5,746,021, and 5,325,626, and references cited therein; and U.S. Pat. App. Pub. Nos. 20020157302, and references cited therein.

In some embodiments, the compounds described herein are used as a repellent, e.g., applied to or in an area in which the presence of ants is not desired. The area can be, e.g., an indoor or outdoor area, in which case the compounds can be delivered generally, e.g., in a spray, powder, granule, gel, or other format. In some embodiments, the area is the skin of a person or animal, and the compounds are applied directly to the skin, e.g., a part of a composition comprising one or more cosmetically acceptable carriers, e.g., in a cream, spray, powder, or lotion as are known in the art.

In general the present compounds will be delivered in an amount effective for the intended purpose, e.g., ant control (by modulation of ant behaviour), and can be delivered directly onto an area known or evident of ant infestation, e.g., directly onto an ant colony, or near an area known or suspected of ant infestation, e.g., onto an agricultural, residential or commercial area in which ant control is desirable.

The compounds, compositions, and formulations described herein can be used in methods for controlling ants, e.g., ants of the subfamily Myrmicinae. For example, the methods can be used to control *Monomorium, Myrmicaria, Solenopsis, Megalomyrmex, Trachymyrmex, Cyphomyrmex,* and *Atta*, including any of the species described herein, e.g., the species listed in Table 3.

EXAMPLES

The invention is further described in the following examples, which do not limit the scope of the invention described in the claims.

Example 1. Isolation and Characterization of Tyramides in *Monomorium, Myrmicaria*, and *Solenopsis*

In the summer of 1995 and 1996, males of the small black ant *Monomorium* minimum Buckley, common in the eastern United States, were collected from nests in Lexington, Va.

Two collections of *Monomorium* minimum Buckley males were collected in July of 1995 and again in July 1996 in Lexington, Va. In each collection 10-20 individuals were obtained and placed in vials containing a small amount of methanol for analysis. One of the 1996 collections was frozen while still alive, the frozen ants were trisected and their heads, thoraxes and gasters were placed in separate vials containing a small amount of methanol. A collection of *M. ebinenum* Forel males was made in Guaynabo, Puerto Rico (PR) in June, 1996, another in July, 1996 and a third collection was made in July, 2003 in Cayey, PR. One of the 1996 collections of *M. ebeninum* was trisected and their heads, thoraxes and gasters were placed in separate vials containing a small amount of methanol. *M. floricola* Jerdon males were collected on 25 May 1999 in Guaynabo, PR. *M. pharaonis* L. males were collected in Gainesville, Fla., and these ants were placed in vials containing a small amount of methylene chloride for analysis. *Myrmicaria opaciventris* workers, males and queens were collected in March, 2003 in Kakamega Dist., Isecheno, Kakamega Forest, Kenya, and placed in vials containing methanol. *Solenopsis* nr *molesta* were collected in 1993 in Chuckawalla Mtns., Red Cloud Cyn. @ 8 mi. SSE. Desert Center, Riverside County, Calif. *Solenopsis maboya* Snelling were collected in Guaynabo, PR in 1999 and 2000, *Solenopsis* #11 males were collected May 8, 1995 near Guaynabo, PR, and *Solenopsis* #78 males were collected Jun. 10, 1998 near Guaynabo, PR. The distribution of tyramides found in these species is shown in Table 1. Voucher specimens have been deposited in the entomological collection of the Los Angeles County Natural History Museum.

General Experimental Procedures were as follows. Gas chromatography-mass spectrometry (GC-MS) was carried out in the EI mode using a Shimadzu QP-5000 GC-MS equipped with an RTX-5, 30 m×0.25 mm i.d. column. The instrument was programmed from 60° C. to 250° C. at 10°/min. Vapor phase FTIR spectra were obtained using a Hewlett-Packard model 5965B detector interfaced with a Hewlett-Packard 5890 gas chromatograph fitted with a 30 m×0.25 mm RTX-5 amine column and a temperature program from 100° C. to 280° C. at 10° C./min or occasionally slower ramps. Some work used a Phenomenex "Inferno" column (30 m×0.22 mm). NMR spectroscopy was carried out in CDCl$_3$ solutions using a Varian Mercury 400 NMR spectrometer. HRMS was performed on a JEOL SX102 instrument in the positive-ion fast-atom bombardment mode using a direct probe and a Waters LCT Premier Time of Flight instrument in the electrospray (ESI) or APCI mode.

The initial GC-MS analysis of CH$_2$Cl$_2$ extracts of these specimens revealed the to presence of two compounds, 3 and 7c, whose mass spectra had an m/z=120 (100) and a significant ion at m/z 107. In one experiment, trisection of *M. minimum* revealed by GC-MS that these compounds occurred in the gaster of the ants. Subsequently, males of the other species listed in Table 1, below, were examined. Trisection of *M. ebeninum* showed that these compounds also were found only in the gasters of the ants. Extracts of whole ants only were available for the remaining species.

In *M. minimum*, the first component had the following GC-FTIR spectrum: $\nu_{max}$ 3652, 3466, 3016, 2968, 2936, 2887, 1707(s), 1613, 1500(s), 1443, 1332, 1256, 1173, 1106, 821 cm$^{-1}$; EIMS m/z 207 [M$^{+\cdot}$] (2), 164 (1), 121 (13), 120 (100), 107 (41), 91 (1), 88 (24), 77 (22), 71 (36), 55 (5), 43 (77), 41 (25). HRMS m/z 207.1254, calcd for $C_{12}H_{17}NO_2$, 207.1259. Its mass spectrum and GC retention time (20.0 min) were identical to those of an authentic sample of N-[2-(4-hydroxyphenyl)ethyl]butanamide (3) (Halmekoski and Pekkala, Acta Pharm. Fenn. 1977, 86, 209-214).

The second and roughly equimolar component at $R_T$ 21.0 min had an EIMS m/z 249 [M$^{+\cdot}$] (2), 234 (1), 206 (1), 164 (4), 121 (35), 120 (100), 107 (22), 91 (9), 85 (13), 77 (18), 57 (40), 43 (8), 41 (20). Initially, it was assumed that this component was a three-carbon homolog of 3; however, the high-resolution mass spectrum (HRMS m/z 249.1361, calcd for $C_{14}H_{19}NO_3$, 249.1365) indicated the presence of a third oxygen and another double bond equivalent. The GC-FTIR of this component had $v_{max}$ 3652, 3429, 3019, 2968, 2938, 2885, 1707(s), 1614, 1513(s), 1439, 1365, 1336, 1258, 1172, 1102, 820 cm$^{-1}$ The frequency (3429 cm$^{-1}$) of the secondary amide NH of this component was shifted to a lower frequency by 37 cm$^{-1}$ suggesting that an intramolecular hydrogen-bond was present. The lack of an obvious infrared absorption for the third oxygen, e.g. a ketone or epoxide functionality, presumed to be in the acyl portion of the amide, was perplexing. The six double bond equivalents determined from the HRMS in comparison with five found for 3 could be consistent with 1) a hydroxyl group and double bond, 2) an epoxide 3) a ketone or 4) a ring with an ether oxygen. No additional hydroxyl frequency was observed in addition to the sharp phenolic $v_{OH}$ at 3652 cm$^{-1}$ nor was any internal or terminal olefinic $v_{=CH}$ absorption noted, ruling out the first possibility. No unambiguous absorptions for an epoxide could be ascertained, but an α-keto group in the acyl moiety could not be excluded since a few published examples had that absorption coupled to the ester or amide absorption and sometimes showed up as a single absorption band (The Aldrich Library of FT-IR Spectra, Vapor Phase Vol. 3, Ed. Pouchert, C. E., Aldrich Chemical Company, Milwaukee, Wis.). Nonetheless it was assumed that an ether $v_{C-O}$ might be present but difficult to detect by IR spectroscopy and consequently three tyramides were synthesized having a cyclic methyl, tetrahydro-furanyl ether, a tetrahydro-pyranyl ether or an α-β epoxide group, all of which might be expected to provide a hydrogen-bond receptor for the observed amide NH donor. This synthetic work and that of other preliminary structural possibilities for the m/z 249 tyramide will be reported elsewhere. None fit the GC-MS or GC-FTIR behavior of the m/z 249 tyramide so the structural possibility 4) above, although biosynthetically attractive, was made less likely. Not all permutations of cyclic ethers were synthesized since about this time it was discovered by a close examination of the amide ramide II band ratio in the m/z 249 tyramide infrared spectrum, the likely presence of a ketone group in the acyl group, most probably in the α-position. This conclusion arose from observing that the ratio of the amide I to amide II bands in the natural MW 249 tyramide was appreciably greater than that seen in 3 as well as those seen with all of the other non-α-keto-tyramides, where the amide II band at 1500-1505 cm$^{-1}$ was significantly more intense than the amide I band. It was therefore concluded that the stretching vibration of the α-keto group coincides with that of the amide $v_{C=O}$ group, enhancing its intensity, and is an example of the "coupling effect" that has been reported for amides (Nakanishi, Infrared Absorption Spectroscopy-Practical., Holden-Day, San Francisco, 1962 p. 19). The above mentioned shift in the amide NH to a lower frequency that suggested H-bonding to an oxygen function, is consistent with an α-keto group being an H-bond acceptor.

Small amounts of the α-ketoamides (7a-c) for GC/MS and GC-FTIR spectroscopic comparison with the natural α-ketoamide were prepared by careful oxidation of the corresponding α-hydroxyamides (8a-c) with the Jones reagent at 0° C. (Scheme 1).

Scheme 1.

8a, R = n-Bu
b, R = 2-Bu
c, R = i-Bu

7a, R = n-Bu
b, R = 2-Bu
c, R = i-Bu i. EDCl, HOBT, DMF
ii. ii. Jones or $V_2O_5$, toluene, Δ

The hydroxyamides 8a-c formed nearly quantitatively by coupling 2-hydroxyhexanoic acid, 2-hydroxy-3-methylpentanoic acid, or 2-hydroxy-4-methylpentanoic acid[14] with tyramine in the presence of EDCI/HOBT. Numerous oxidation methods of the hydroxyamides were attempted, including PCC, PDC, $CrO_3$ on celite, chromic acid/ether, Swern oxidation, and Dess-Martin periodane but the Jones reagent at 0° C. for 10 min., although providing low yields (10-20%) gave clean samples of the α-ketoamides after flash chromatography. A great improvement in the oxidations of 8a and 8c was achieved by air-oxidation with a catalytic amount of $V_2O_5$ in toluene at 90-100° C. (Velusamy and Punniyamurthy, Org. Lett. 2004, 6, 217-219) where 7a and 7c were obtained respectively in ca. 60% yield after chromatography.

The straight-chain analog (7a) was first synthesized and found non-identical with the natural tyramide but it was recognized by close inspection of the expanded $v_{C-H}$ region (see FIG. 1), that the asymmetric vibration at ca. 2960 cm$^{-1}$ relative to the $v_{C-H}$ methylene stretching vibration indicated that another methyl group was clearly present in the acyl moiety of the natural tyramide. This "methyl-counting" method had earlier been applied by one of us (H.M.G) to the assignment of a tentative structure to a novel homo-pumiliotoxin alkaloid 249F found in an Argentine toad (Daly et al., Toxicon 2008, 52, 858-870).

Figure 2:
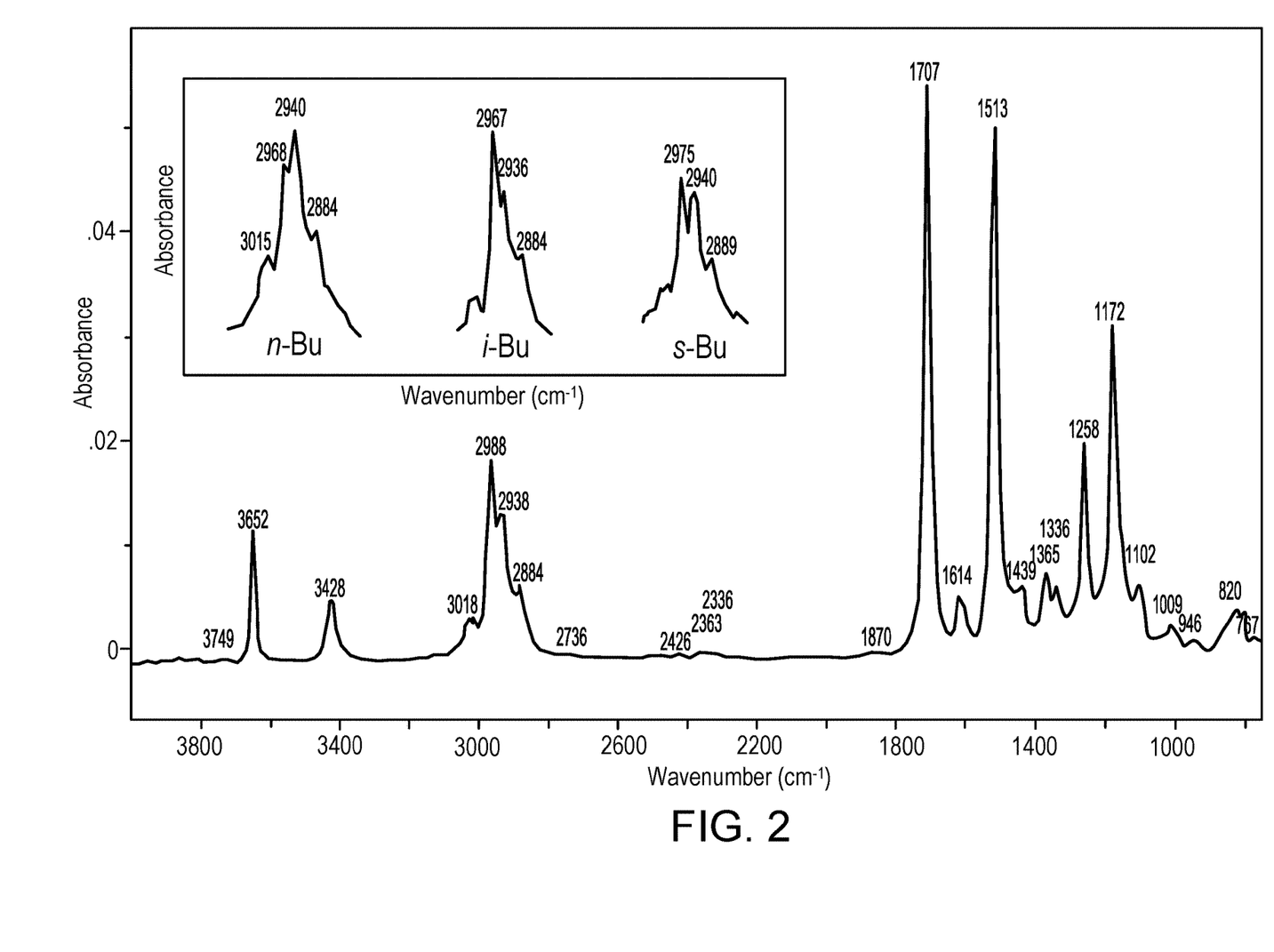
FIG. 2 is an FTIR vapor-phase spectrum of the natural α-ketotyramide from males of the ant *M. miminum*. Insets are of the VCH regions of synthetic 7a, 7c, and 7b from left to right.

The methylene bending vibrations at ca. 1385 cm$^{-1}$ gave no clear evidence of a gem dimethyl group so a 2-keto-3-methyl pentanoyl tyramide (7b) was then synthesized. Although very similar in MS and IR spectra, it was not identical with the natural tyramide leaving a 2-keto-4-methylpentanoyl tyramide (7c) as the remaining likely structural possibility for the m/z 249 tyramide. Synthesis of 4-methyl 2-keto pentanoyl tyramide (7c) finally revealed that the natural m/z 249 tyramide possessed that structure, despite the fact that the gem dimethyl absorption, expected for such an "iso" structure is not unambiguously evident. The mass spectrum, gas chromatographic retention time and GC-FTIR spectrum of the natural tyramide matched that shown for 7c in FIG. 2.

Evidence for oxygen functionality at the α-position of the tyramide acyl moiety was also deduced from the EI mass spectrum of the natural m/z 249 tyramide where a cleavage between the acyl amide C=O and the adjacent ketone carbon is seen giving an m/z 85 (12%) fragment and a related weak but diagnostic fragment at m/z 164 (2.4%) is seen as an indication that both cleavage fragments carry charge. No cleavage for 7c is seen between the acyl carbonyl and the amide nitrogen yielding a minor or even significant fragment ion at m/z 130 that is seen in all the other tyramides lacking an α-keto- or α-hydroxyl-substituent. The major fragments of all the tyramides are governed by cleavage at the benzylic position to afford the m/z 107 ion (ca. 40%) and a McLafferty rearrangement to yield as the base peak, the m/z 120 ion, having a p-hydroxystyrene structure.

After the structures of 3 and 7c were established in males of M. minimum and M. ebeninum, extracts of the other male ants listed in Table 1 were examined and the structures of tyramides 2, 3, and 4 were determined by spectral analyses and comparison with synthetic material (Halmekoski and Pekkala, Acta Pharm. Fenn. 1977, 86, 209-214; Halmekoski et al., Acta Pharm. Fenn. 1979, 88, 73-78).

TABLE 1

Distribution of Tyramides from Myrmicine ants.

| Species | Dates collected | 2 | 3 | 4 | 7c |
|---|---|---|---|---|---|
| Monomorium minimum | 1995 & 1996 | | | * | * |
| Monomorium ebeninum | 1996 & 2003 | | | * | * |
| Monomorium floricola | 1999 | | | * | |
| Monomorium pharaonis | 1999 | | | | * |
| Myrmicaria opaciventris | 2003 | | * | | |
| Solenopsis nr. molesta | 1993 | | * | | |
| Solenopsis #11 PR | 1995 | | | | * |
| Solenopsis #78 PR | 1998 | | | | * |
| Solenopsis maboya | 1999 & 2000 | | | | * |

Example 2. Synthetic Methods for 8a, 8b, and 8c

N-[2-(4-Hydroxyphenyl)ethyl]-2-hydroxyhexanamide (8a)

A solution containing 0.26 g of 2-hydroxyhexanoic acid (Shin et al., J. Org. Chem. 2000, 65, 7667-7675) (2 mmol), 0.26 g of tyramine, 0.27 g of 1-hydroxy-benzotriazole (HOBT) and 0.4 g of N-ethyl-N-(3-dimethylaminopropyl) carbodiimide (EDCI) in 8 mL of DMF was stirred overnight at room temperature. The solvent was removed under reduced pressure and the residue was partitioned between 2% HCl and diethyl ether. The ether layer was dried over anhydrous MgSO$_4$. After filtration, the solvent was removed to provide 0.55 g of 8a, $^{13}$C NMR (100 MHz, d$_6$DMSO) δ 174.54, 156.31, 130.08 (2C), 130.05, 115.76 (2C), 71.61, 35.11, 34.74, 27.46, 22.74, 14.57, (the CH$_2$NH signal was obscured by the solvent); EIMS m/z 251 [M$^+$] (1), 194 (1), 164(1), 132 (4), 121 (17), 120 (100), 107 (12), 91 (3), 77 (6), 69 (5). HRMS m/z 251.1570; calcd for C$_{14}$H$_{21}$NO$_3$, 251.1521.

N-[2-(4-Hydroxyphenyl)ethyl]-2-hydroxy-3-methylpentanamide (8b)

A solution containing 0.26 g of 2-hydroxy-3-methylpentanoic acid (Shin et al., J. Org. Chem. 2000, 65, 7667-7675) (2 mmol) was condensed with tyramine as described for 8a to provide 0.8 g of a mixture that was 70% pure, the remainder being benzotriazole. $^1$H NMR (400 MHz, d$_6$-DMSO) δ 7.29 (5H, m), 4.48 (1H, t, J=5.2 Hz), 4.09 (2H, dd, J=11.6 and 5 Hz), 3.75 (4H, m), 2.78 (2H, m), 2.60 (1H, m), 2.07 (1H, m), 1.8-1.4 (13H, br. m); $^{13}$C NMR (100 MHz, d$_6$DMSO) δ 173.77, 156.27, 130.11 (2C), 130.08, 115.74 (2C), 75.72, 38.72, 35.11, 23.69, 16.31, 12.44, (CH$_2$NH buried under the solvent signal); EIMS m/z 251 [M$^+$] (1), 194 (2), 164(2), 132 (6), 121 (17), 120 (100), 107 (11), 91 (4), 77 (8), 45 (9). HRMS m/z 251.1543; calcd for C$_{14}$H$_{21}$NO$_3$, 251.1521.

N-[2-(4-Hydroxyphenyl)ethyl]-2-hydroxy-4-methylpentanamide (8c)

A solution containing 0.26 g of 2-hydroxy-4-methylpentanoic acid (Shin et al., J. Org. Chem. 2000, 65, 7667-7675) (2 mmol) was condensed with tyramine as described for 8a. $^{13}$C NMR (100 MHz, d$_6$-DMSO) δ 174.93, 156.28, 130.14 (2C), 130.1, 115.75 (2C), 70.22, 44.17, 35.08, 24.54, 24.12, 22.20. (CH$_2$NH buried under the solvent signal). EIMS m/z 251 [M$^+$] (1), 194 (1), 164(2), 132 (3), 121 (16), 120 (100), 107 (13), 91 (3), 77 (6), 45 (1), 43 (6). HRMS m/z 251.1521; calcd for C$_{14}$H$_{21}$NO$_3$, 251.1521.

Example 3. Synthetic Methods for 7a, 7b, and 7c

N-[2-(4-Hydroxyphenyl)ethyl]-2-oxohexanamide (7a)

A solution containing 60 mg of 5a in 3 mL of toluene and 20 mg of $V_2O_5$ was heated at 100° C. overnight. The cooled solution was filtered through a short column of florisil to provide 45 mg of 7a that was more than 75% pure by GC-MS analysis. No starting material remained. $^1$H NMR (400 MHz, CDCl$_3$) δ 6.93 (2H, d, J=8.2 Hz), 6.74 (2H, d, J=8.2 Hz), 3.43 (2H, q, J=5 Hz), 3.41, (1H, m), 2.83 (2H, t, J=7 Hz), 2.68 (2H, t, J=6.8 Hz), 2.1 (1H, s), 1.5 (2H, quintet, J=7 Hz), 1.25 (2H, sextet, J=7 Hz), 0.82 (3H, t, J=7.1 Hz); $^{13}$C NMR (100 MHz, CDCl$_3$) δ 198.18, 159.17, 153.71, 128.84 (2C), 128.84, 114.63 (2C), 39.72, 35.44, 33.49, 24.20, 21.15, 12.79; EIMS m/z 249 [M$^+$] (1), 164 (5), 121 (30), 120 (100), 107 (25), 91 (6), 85 (9), 77 (13), 57 (20). CI-HRMS [M+H]$^+$ m/z 250.1445; calcd for $C_{14}H_{20}NO_3$, 250. 1443.

N-[2-(4-Hydroxyphenyl)ethyl]-3-methyl-2-oxopentanamide (7b)

A solution containing 0.5 g (2 mmol) of crude 8b in 20 mL of acetone was cooled to 0° C. and treated with 2 mL of Jones' reagent. After 15 min, 3 mL of 2-propanol was added and the solution was taken up in 50 mL of ether. The solution was dried over anhydrous MgSO$_4$, filtered and the solvent was removed under reduced pressure. Flash chromatography with silica gel (hexane/ethyl acetate) provided 60 mg of 7b for spectroscopic analysis. $^1$H NMR (400 MHz, CDCl$_3$) δ 6.97 (2H, d, J=8.2 Hz), 6.72 (2H, d, J=8.2 Hz), 3.44 (2H, q, J=5 Hz), 3.41, (1H, m), 2.70 (2H, d, J=7 Hz), 2.7 (2H, J=6.8 Hz), 2.08 (1H, m), 1.01 (2H, d, J=7 Hz), 0.81 (3H, t, J=7.1 Hz); $^{13}$C NMR (100 MHz, CDCl$_3$) δ 201.19, 159.08, 153.90, 128.75 (2C), 128.67, 114.63 (2C), 39.82, 39.37, 33.50, 24.38, 14.07, 10.45; EIMS m/z 249 [M$^+$] (1), 164 (7), 121 (42), 120 (100), 107 (16), 91 (6), 85 (10), 77 (11), 57 (50). CI-HRMS [M+H]$^+$ m/z 250.1442; calcd for $C_{14}H_{20}NO_3$, 250.1443

N-[2-(4-Hydroxyphenyl)ethyl]-4-methyl-2-oxopentanamide (7c)

A solution with the same amounts of reactants as-described for 7a provided 46 mg of 7c after flash chromatography. $^1$H NMR (400 MHz, CDCl$_3$) δ 6.97 (2H, d, J=8.2 Hz), 6.72 (2H, d, J=8.2 Hz), 3.44 (2H, q, J=5 Hz), 5.7 (2H, br m) 2.7 (2H, t, J=6.8 Hz), 2.08 (1H, m), 0.86 (6H, d, J=6.8 Hz); $^{13}$C NMR (100 MHz, CDCl$_3$) δ 199.06, 160.48, 154.83, 130.24, 130.03 (2C), 115.84 (2C), 45.48, 40.96, 34.75, 24.58, 22.75 (2C). EIMS m/z 249 [M$^+$] (3), 164 (7), 121 (37), 120 (100), 107 (20), 91 (3), 85 (9), 77 (9), 57 (25), 41 (8). CI-HRMS [M+H]$^+$ m/z 250.1443; calcd for $C_{14}H_{20}NO_3$, 250.1443.

The gas chromatographic retention time, mass spectrum and FTIR spectrum of 7c were identical to those of the α-oxotyramide found in M. minimum, M. ebeninum, and M. pharaonis, confirming the identity of the naturally-occurring compound.

Example 4. Isolation and Characterization of Tyramides in Megalomyrmex, Trachymyrmex, and Cyphomyrmex Two ant tribes are represented in this study, Solenopsidini (Megalomyrmex modestus, Megalomyrmex wallacei, Megalomyrmex wettereri, Megalomyrmex symmetochus, and Megalomyrmex staudingeri) and Attini (Cyphomyrmex faunulus and Trachymyrmex septentrionalis). All species occur in wet Neotropical rainforests in Central and South America besides T. septentrionalis which occurs in the Midwestern, Southern and Eastern parts of the United States (Rabeling et al., Zootaxa 1664:1, 2007). M. modestus and M. wallacei were collected at two sites in Costa Rica (10.33333N, 84.08333W and 10.4264N, 84.0258W, respectively), M. staudingeri in Peru (3.44S, 72.85W), M. wettereri and M. symmetochus in Panama (9.120858N, 79.715906W), T. septentrionalis in the United States (37.37057N, 78.683217W), and C. faunulus in Suriname and French Guiana (4.73019444N, 56.768Wand 4.08835N, 52.67718W, respectively) (Table 1). M. modestus, M. staudingeri and M. wallacei are free-living species while M. wettereri and M. symmetochus associate with fungus-growing ant species (Adams et al., Naturwissenschaften 87, 549, 2000; Brandão, Arq. Zool. São Paulo 31:411, 1990; Brandão, Pap. Avuls. Zool. 43:145, 2003). T. septentrionalis and C. faunulus are fungus-growing ants that maintain a symbiotic relationship with their fungal cultivar and are in two distinct phylogenic clades (Schultz and Brady, Proc. Natl. Acad. Sci. U.S.A. 105:5435, 2008). Voucher specimens have been deposited at the Smithsonian Institution National Museum of Natural History, Washington, D.C.

Two to 15 winged males of the above mentioned species were taken from live colonies from the field or laboratory and placed in 100% methanol. Gas chromatography-mass spectrometry was carried out in the EI mode using a Shimadzu QP 2010 GC/MS equipped with a RTX-5, 30 m×0.25 mm i.d., column. The instrument was programmed from 60° C. to 250° C. at 10°/min. High-resolution mass spectrometry was performed on a Waters GCT high-resolution mass spectrometer (using an electron impact volume) coupled to an Agilent HP-6890 series GC system, using a Restek RTX-5MS (5% diphenyl-95% dimethyl polysiloxane, 30 m length, 0.25 mm ID, 0.25 um film thickness) column operating with a temperature program of 100° C. (1 min) to 280° C. (10 min) at a rate of 10° C./min, and with a constant flow of He of 1 ml/min as the gas carrier.

The previously described tyramides (R=CH$_3$ (1), n-C$_3$H$_7$ (3)) were identified by direct GC/MS comparison with authentic samples (Böröczky et al., Chem. Biodivers. 3:622, 2006; Jones et al., 2010). N-[2-(4-hydroxyphenyl)ethyl]hexanamide (R=n-C$_5$H$_{11}$ (6)) was suggested by its mass spectra: EIMS m/z 235 (2), 121 (13), 120 (100), 116(12), 107 (40), 99 (3), 91 (1), 77 (2), 71 (7), 43 (16); HRMS m/z 235.1573 calcd. for C$_{14}$H$_{21}$NO$_2$ 235.1572. It was identical in every respect to an authentic sample prepared by the condensation of tyramine with hexanoyl chloride (Janusz et al., J. Med. Chem. 36:2595, 1993). The results of this investigation are summarized in Table 2.

ered major pests: *S. invicta*, the imported fire ant, and *A. cephalotes*, a leaf cutter ant. *S. invicta* are extremely voracious and can wreak economically significant damage to crops, foliage, livestock, and agricultural operations. Aggressive when disturbed, fire ants will swarm and sting the source of the disturbance, with burning and itching lesions commonly resulting. Large infestations of *A. cephalotes* are able to defoliate entire orchards or forests practically overnight.

Methods similar to those described above for Examples 1 and 4 were used.

TABLE 2

Male tyramides. Collection number includes the initials of the collector, the date (yr/month/day), and the series. The numbers reported are relative ratios of the compounds and X indicates that only one compound was detected.

| Species | Collection Numbers | 1 CH$_3$ | 3 n-C$_3$H$_7$ | 4 2-C$_3$H$_7$ | 5 2-C$_4$H$_9$ | 6 n-C$_5$H$_{11}$ |
|---|---|---|---|---|---|---|
| *Megalomyrmex modestus* | RMMA030812-01 | | 1.5 | | | 1 |
| *Megalomyrmex mondabora* | RMMA030729-12 | | 9 | | | 1 |
| *Megalomyrmex staudingeri* | RMMA040613-05 | | 1.5 | | | 1 |
| *Megalomyrmex wallecei* | RMMA050710-01 | | 1 | | | 1 |
| *Megalomyrmex wetterei* | RMMA010330-01 | | 2 | | | 1 |
| *Trachymyrmex septentrionalis* | SAR040627-01 | X | | | | |
| *Cyphomyrmex faunulus* | JSC060307-05 | | | X | | |
| | TRS050729-18 | | | | | |
| *Trachymyrmex cornetzi* | RMMA 100521m | | | X | | |
| *Trachymyrmex bugnioni* | RMMA tbugc001m | | | X | X | |

All ants in this and a previous study (Jones et al., J. Nat. Prod. 73:313, 2010) occupy two large phylogenetic clades in the subfamily Myrmicinae (Brady et al., Proc. Natl. Acad. Sci. U.S.A. 103:18172, 2006) and represent three different tribes of ants (Myrmicariini: *Myrmicaria*; Solenopsidini: *Megalomyrmex, Monomorium*, and *Solenopsis*; Attini: *Cyphomyrmex* and *Trachymyrmex*). In the present study, the hexanamide (R=C$_5$H$_{11}$ (6)) and the butanamide (R=C$_3$H$_7$ (3)) are present in males of *Megalomyrmex* in varying ratios that may be species specific, while males of *Cyphomyrmex* has only the butanamide (R=C$_3$H$_7$ (3)) which had been previously reported in *Monomorium* and *Myrmicaria* males. Finally males of *Trachymyrmex septentrionalis* have the acetamide (R=CH$_3$ (1)), while those of *Trachymyrmex cornetzi* have the isobutanamide (R=2-C$_3$H$_7$ (4)) and *Trachymyrmex bugnioni* have the isobutanamide (R=2-C$_3$H$_7$ (4)) and the 2-methylpentanamide (R=2-C$_4$H$_9$ (5)) which have not been previously reported in ants (Table 2). It appears that these tyramides are not ant tribe specific and have none or little phylogenetic signal. *Cyphomyrmex, Monomorium* and *Myrmicaria* are all distant relatives belonging to different ant tribes yet share the same propanamide where as *Cyphomyrmex* and *Trachymyrmex* are both fungus-growing ants and members of the tribe Attini and do not have any amides in common.

Example 5. Isolation and Characterization of Tyramides in *Trachymyrmex, Solenopsis* and *Atta*

The present example describes the presence of tyramides in additional species, including two species that are consid-

TABLE 3

| Species | Collection Numbers | 1 CH$_3$ | 2 C$_2$H$_5$ | 3 n-C$_3$H$_7$ | 6 n-C$_5$H$_{11}$ |
|---|---|---|---|---|---|
| *Trachymyrmex zateki* | | | X | | |
| *Solenopsis invicta* | | 1 | | | 2 |
| *Solenopsis geminata* | | 1 | | | 1 |
| *Atta cephalotes* | RMMA 100615-01m | t | X | | |

As can be seen in table 3, the males of *Trachymyrmex zateki* have the propanamide (R=C$_2$H$_5$ (2)) demonstrating that for this genus, there is considerable variety in the male tyramides. On the other hand, the males of two species of fire ant, *Solenopsis* (*Solenopsis*), have the acetamide (R=CH$_3$ (1)) and the hexanamide (R=C$_5$H$_{11}$ (6)), while males of the leaf cutter ant *Atta cephalotes* have acetamide (R=CH$_3$ (1)) and the propanamide (R=C$_2$H$_5$ (2)).

Example 6. Isolation and Characterization of Tyramides in *Solenopsis*

Novel biologically-based fire ant control methods based on interference or manipulation of biogenic amines and/or their receptors will add biologically-based, environmentally friendly control methods to the arsenal of tools to combat pest ants. The experiments in this example further characterized the anatomical location of the tyramides in fire ants.

Acetyl and hexanoyl tyramide are the tyramides reported to be present in *Solenopsis invicta* male abdomens. Tyramide standards were synthetically prepared as described herein. Butanoyltyramide, not found in *S. invicta*, was used as an internal standard for gas chromatographic analysis. In all cases described below the methanol solvent contained an appropriate amount of butanoyltyramide internal standard.

Mature male alates (winged male sexuals) were used in all experiments. Maturity could only be determined upon dissection and determination of whether or not the male's testes were degenerated. This is the key indicator of maturity. See Ball and Vinson, Int. J. Insect Morphol. Embryol. 13:283-294 (1984) for a description and figure of the fire ant male genitalia. Males were discarded if their testes were not degenerated. Dissection of the male reproductive system was carried out in a drop of water. The entire system included pairs of degenerated testes, seminal vesicle, accessory glands, and the single external genitalia. After dissection of the entire system the three sections were further dissected: A) degenerated testes and seminal vesicle; B) accessory glands; and C) external genitalia. The reproductive system or its parts were placed in methanol and macerated using a fine probe. Methylene chloride was initially used as the solvent, but was found to be a poor solvent for the more polar acetyl tyramide; therefore, methanol containing internal standard was the solvent used to extract tyramides from dissected tissue.

Mature female alates (winged female sexuals) were collected from field colonies or from laboratory reared colonies that originated from field colonies. Weight (>15 mg) was the criteria for maturity. The large amounts of venom alkaloids in the venom sac (male alates do not have a venom sac or sting apparatus) interfere with analysis of the tyramides; therefore, the sting apparatus containing the Dufour's gland, poison gland and sac, and stinger were removed, then the gaster was placed in methanol containing internal standard and a fine probe was used to macerate the tissue.

Newly mated queens (NMQ) were collected immediately after mating flights and placed in a refrigerator to slow development until dissection (less than 18 hours). Newly mated queens were weighed and only NMQs>15 mg were used for dissection. Queens were dissected in a drop of water. The large amounts of venom alkaloids in the venom sac interfere with analysis of the tyramides; therefore, the gaster was opened and the venom sac and digestive tract removed leaving only the female reproductive system in the gaster. See Hermann and Blum, Ann. Entomol. Soc. Am. 58:81-89 (1965) for a description of the reproductive system of the imported fire ant. The gaster containing the reproductive system was placed in a vial, containing methanol with internal standard, and a fine probe was used to macerate the tissue.

Gas Chromatographic analysis was performed as follows. The tyramide components of interest in the samples were separated using a gas chromatograph (GC, Agilent 6890N) equipped with a 30 m×0.25 mm i.d. HP-1 fused silica capillary column. Helium was used as the carrier gas. The GC oven was programmed from 150° C. to 200° C. at 2° C./min, then to 285° C. at 15° C./min and held for 5 min. Eluting components were detected and analyzed on an Agilent Mass Selective Detector 5973 (Palo Alto, Calif.). The GC-MS transfer line was set at 250° C., the source was set at 230° C. and the MS quadruples set at 150° C. The eluting components were identified based on unique retention times and fragmentation patterns. Quantification of the two tyramides was achieved by comparing their total ion area to the total ion area of the Internal Standard.

The results were as follows.

Figure 3:
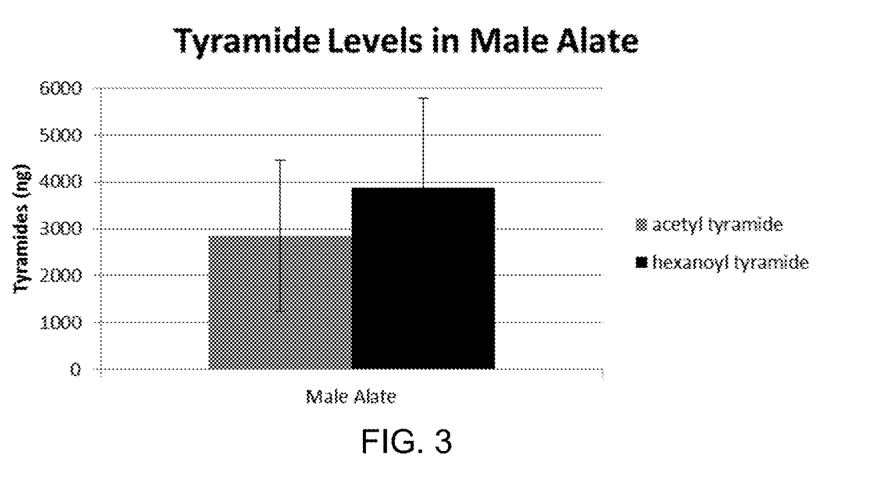
FIG. 3 is a bar graph showing tyramide levels in male alate abdomens/reproductive system expressed as ng/male alate. Mean±SE are shown.

Male Alates. As noted above, the tyramides were previously found only in the abdomens of male alates. In studies when the male reproductive system and the abdomen minus reproductive system were analyzed, the tyramides were only found in the male reproductive system (see FIG. 3). The acetyl tyramide mean±SE was 2.9±1.6 μg and hexanoyl tyramide was 3.9±1.9 μg per male alate.

Figure 4:
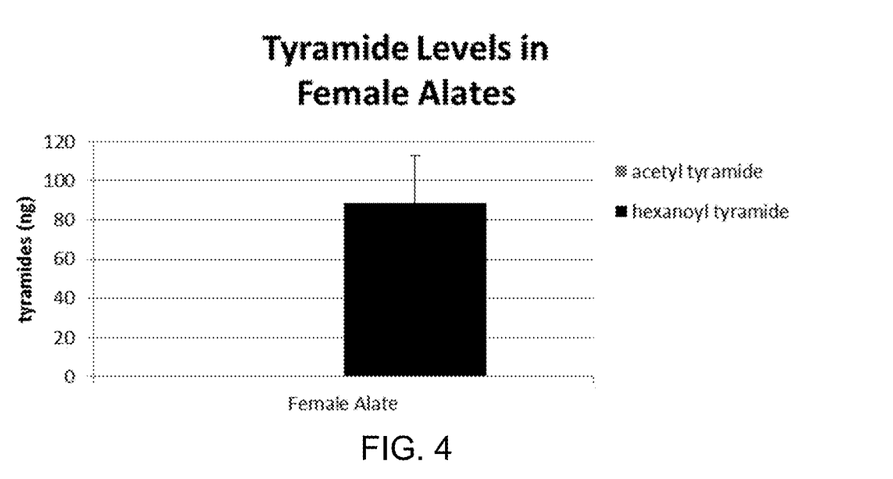
FIG. 4 is a bar graph showing tyramide levels in male alate abdomens/reproductive system expressed as ng/male alate. Mean±SE are shown. The acetyl tyramide was not detectable.
Figure 5:
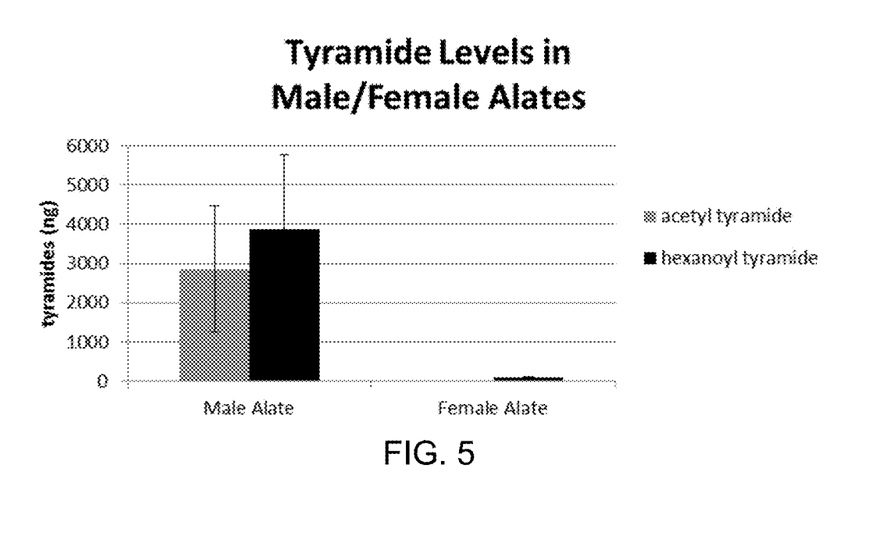
FIG. 5 is a bar graph showing tyramide levels in male and female alate abdomens/reproductive system expressed as ng/alate. Mean±SE are shown. For female alates the acetyl tyramide was not detectable.

Female Alates. Since the tyramides had not been found in female ants (workers or female sexuals) the expectation was that tyramides would be found in low to absent levels in female alates. The poison sac piperidine alkaloids are present in large μg quantities in female alates and interfere with the analysis of the tyramides. Therefore, female alates abdomens were analyzed for tyramides after the poison sac/sting apparatus removal. Results are shown in FIG. 4. For a better sense of the differences between male and female alates the two results are shown in FIG. 5.

Figure 6:
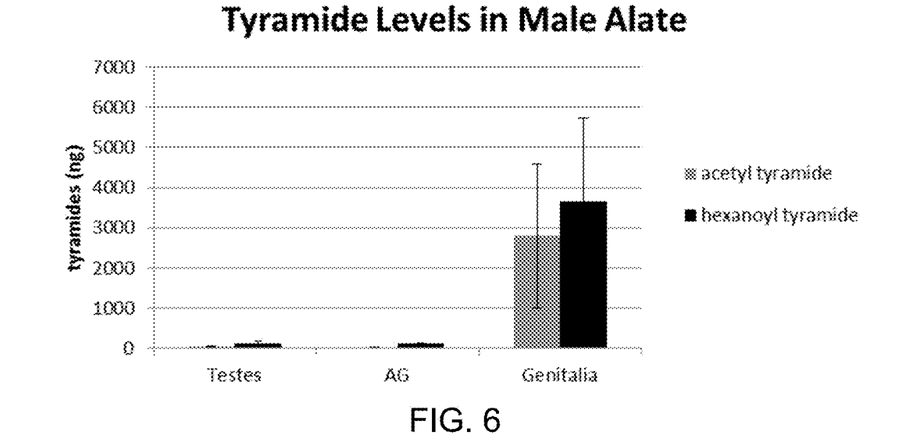
FIG. 6 is a bar graph showing tyramide levels in three sections of the male alate reproductive system: Testes/seminal vesicles; Accessory glands; and external genitalia. Amounts are expressed as ng/male alate. Mean±SE are shown.

Male Reproductive System Parts. Since the tyramides were found in direct association with the Male reproductive system and this system has 3 distinct dissectible parts, it was of interest to determine if the tyramides were associated with all parts or a specific part of the genitalia. FIG. 6 shows the results of these analyses. Low-level amounts of both tyramides were found in the testes/seminal vesicles and the accessory glands; however, large amounts of the tyramides were found in the external genitalia. That these compounds are strongly associated with only one part of the male reproductive system, specifically the external genitalia, suggests a function either during mating via transfer to the female and/or delayed action directed at the new queen after mating. It was of interest to determine if male tyramides were transferred from male to female during mating.

Figure 7:
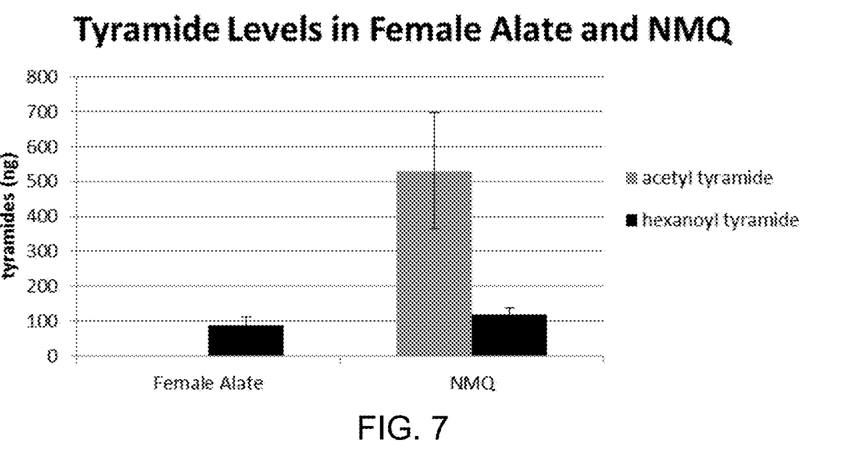
FIG. 7 is a bar graph showing tyramide levels in female alate and newly mated queen reproductive systems. Amounts are expressed as ng/individual. Mean±SE are shown.
Figure 8:
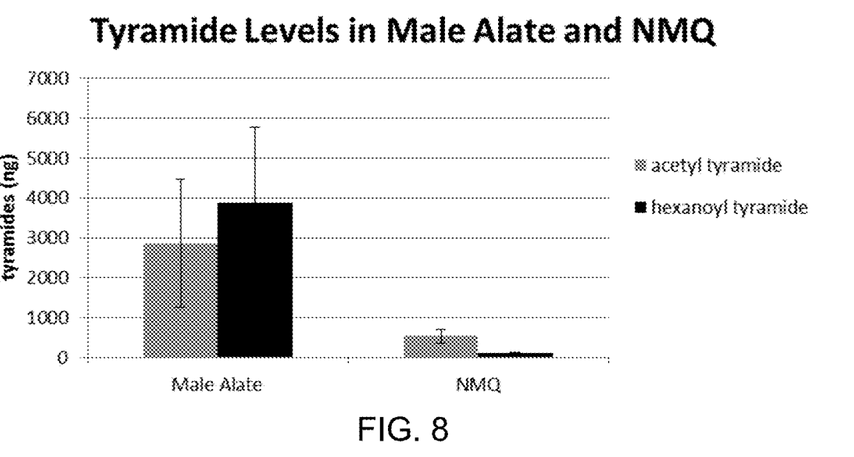
FIG. 8 is a bar graph showing tyramide levels in male alates compared to levels transferred to newly mated queens during mating flights. Amounts are expressed as ng/individual. Mean±SE are shown.

Transfer of Tyramides. Newly mated queen abdomens minus poison sac and digestive system were analyzed for the tyramides soon after mating. The results are shown in FIG. 7. The results clearly show that the tyramides are transferred to females during the mating process. Interestingly, the acetyl to hexanoyl tyramide ratio in the NMQ is very different from that found in the males. This suggests that there is preferential absorption of the hexanoyl tyramide, since the male likely cannot transfer one without the other. Also, the total amount of tyramides in NMQs is significantly lower than what is in the males (see FIG. 8), which indicates that the transfer is inefficient or more likely that the tyramides are quickly absorbed to the hemolymph where they may function as neuromodulators, as has been shown for biogenic amines, e.g., tyramine and octopamine.

ADDITIONAL REFERENCES (1) Jones et al., Tetrahedron 1982, 38, 1949-1958.
(2) Numata, A.; Ibuka, T. in The Alkaloids; Brossi, A. Ed.; Academic Press; New York, 1987; 31, pp 193-315.
(3) Jones et al., J. Chem. Ecol. 1991, 17, 2507-2517.
(4) Jones et al., J. Nat. Prod. 2007, 70, 160-168.
(5) Deslippe and Guo, Toxicon 2000, 38, 223-232.
(6) Spande et al., J. Nat. Prod. 1999, 62, 5-21.
(7) Tones et al., Sociobiology, 2001, 37, 579-583.
(8) Jones et al., J. Nat. Prod. 1996, 59, 801-803.
(9) Schroder et al., Tetrahedron 1996, 52, 13539-13546.
(10) Böröczky et al. Chem. Biodiv. 2006, 3, 622-634.
(11) Smith et al., J. Cold Spring Harb. Protoc. 2009, 4, 1-13.
(12) Blum et al., M. Comp. Biochem. Physiol., 1987, 86B, 251-252.
(13) Brand et al., Science 1973, 179, 388-389.
(14) Kenne and Dejean, Sociobiology 1998, 31, 41-50.
(15) Snelling, Sociobiology 2001, 37, 511-525.
(16) Noordijk et al., Insect. Soc. 2008, 55, 266-273.
(17) Adams et al., Biochem. Sys. Ecol. 2010, 38, 454-456.
(18) Jones et al., J. Nat. Prod. 2010, 73, 313-31.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of disrupting reproduction of ants, the method comprising administering to the ants an amount of a composition effective to disrupt reproduction, wherein the composition comprises one or more compounds of a formula selected from the group consisting of:

Formula I

Formula II

Formula III wherein R and R' can be a branched, unbranched, cyclic, polycyclic, or unsaturated carbon or cyclic ether moiety up to twenty carbons, or a salt thereof, and wherein the ants are members of a genus selected from *Monomorium, Myrmicaria, Megalomyrmex, Trachymyrmex,* and *Cyphomyrmex.*

2. The method of claim 1, wherein the composition further comprises an ant-attractant component, an ant-toxic component, or both.

3. The method of claim 1, wherein the composition is substantially purified.

4. The method of claim 1, wherein the compound is in a solid, liquid, or semi-solid form.

5. The method of claim 4, wherein the composition is a spray, powder, granule, tablet, gel, cream, or lotion.

6. The method of claim 1, wherein the salt is a sodium, potassium, or ammonium salt.

7. The method of claim 1, wherein the composition is administered before the annual mating time period of the ants.

8. The method of claim 7, wherein the compositions is administered from about 24 hours to about 1 month before the annual mating time period of the ants.

* * * * *

UNITED STATES PATENT AND TRADEMARK OFFICE
CERTIFICATE OF CORRECTION

PATENT NO. : 11,767,289 B2
APPLICATION NO. : 15/419899
DATED : September 26, 2023
INVENTOR(S) : Tappey H. Jones and Robert Kenneth Vander Meer It is certified that error appears in the above-identified patent and that said Letters Patent is hereby corrected as shown below:

In the Specification

Column 2, Line 8, delete "Biochem," and insert -- Biochem. --

Column 2, Line 15, delete "53(2)487-194." and insert -- 53(2):187-194. --

Column 2, Line 31, delete "(Dalia" and insert -- (Dalla --

Column 2, Line 44, delete "(Melanophiyniscus),"" and insert -- (Melanophryniscus)," --

Signed and Sealed this
Fifth Day of December, 2023

Katherine Kelly Vidal
*Director of the United States Patent and Trademark Office*